United States Patent
Scheckel

(10) Patent No.: US 9,649,475 B2
(45) Date of Patent: *May 16, 2017

(54) CATHETER DEVICE HAVING A CATHETER AND AN ACTUATION DEVICE

(71) Applicant: ECP ENTWICKLUNGSGESELLSCHAFT MBH, Berlin (DE)

(72) Inventor: Mario Scheckel, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/807,484

(22) Filed: Jul. 23, 2015

(65) Prior Publication Data
US 2016/0051795 A1 Feb. 25, 2016

Related U.S. Application Data

(63) Continuation of application No. 13/147,880, filed as application No. PCT/EP2010/000952 on Feb. 3, 2010, now Pat. No. 9,089,670.
(Continued)

(30) Foreign Application Priority Data

Feb. 4, 2009 (EP) .................................... 09075053

(51) Int. Cl.
*A61M 25/01* (2006.01)
*A61M 1/10* (2006.01)
(Continued)

(52) U.S. Cl.
CPC ........ *A61M 25/0113* (2013.01); *A61M 1/101* (2013.01); *A61M 1/1024* (2014.02);
(Continued)

(58) Field of Classification Search
CPC .... A61M 1/10; A61M 1/1001; A61M 1/1008; A61M 1/1024; A61M 1/1029
(Continued)

(56) References Cited

U.S. PATENT DOCUMENTS 3,510,229 A 5/1970 Smith et al.
3,568,659 A 3/1971 Karnegis
(Continued)

FOREIGN PATENT DOCUMENTS

CA 1008330 A 4/1977
CA 2311977 A1 12/2000
(Continued)

OTHER PUBLICATIONS

International Preliminary Report on Patentability mailed Aug. 9, 2011 in connection with PCT/EP2010/000952.

*Primary Examiner* — Paula J Stice
(74) *Attorney, Agent, or Firm* — White & Case LLP

(57) ABSTRACT

The invention relates to a catheter device, having a catheter (1), an actuation device (8) at a first end of the catheter and also a mechanical transmission element (9, 10) for transmitting a movement along the catheter to the actuation device, the actuation device having a coupling element (14) which is connected to the transmission element (9, 10) and can be actuated by the latter relative to the longitudinal direction of the catheter in a first degree of freedom, and also a conversion element (15) which can be actuated by the coupling element and which converts the actuation movement at least partially into a movement in a second degree of freedom. As a result, a combined movement at the distal end of the catheter can be produced particularly simply for compression and release of a functional element.

17 Claims, 3 Drawing Sheets

Related U.S. Application Data

Figure 1:
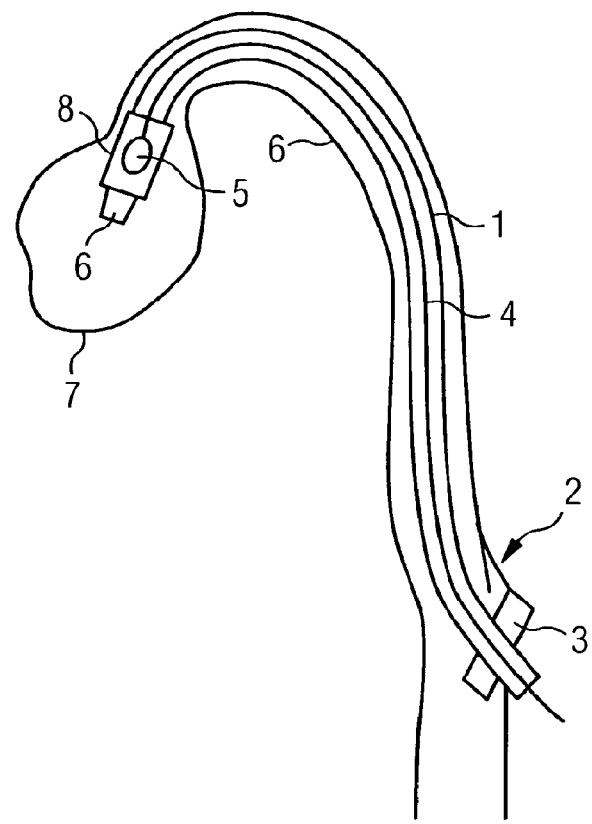

(60) Provisional application No. 61/149,753, filed on Feb. 4, 2009.

(51) Int. Cl.
 *A61M 1/12* (2006.01)
 *A61M 25/06* (2006.01)
 *A61M 25/00* (2006.01)

(52) U.S. Cl.
 CPC .......... *A61M 1/1034* (2014.02); *A61M 1/125* (2014.02); *A61M 25/0082* (2013.01); *A61M 25/0147* (2013.01); *A61M 25/0662* (2013.01); *A61M 25/0074* (2013.01); *A61M 2025/015* (2013.01); *A61M 2210/125* (2013.01)

(58) Field of Classification Search
 USPC .......................................................... 607/16
 See application file for complete search history.

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,934,909 B2 | 5/2011 | Nuesser et al. |
| 9,089,670 B2 * | 7/2015 | Scheckel |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

(56) References Cited

U.S. PATENT DOCUMENTS

FOREIGN PATENT DOCUMENTS

| | | | |
|---|---|---|---|
| CA | 2701809 | A1 | 4/2009 |
| CA | 2701810 | A1 | 4/2009 |
| DE | 2207296 | A1 | 8/1972 |
| DE | 2113986 | A1 | 9/1972 |
| DE | 2233293 | A1 | 1/1973 |
| DE | 2613696 | A1 | 10/1977 |
| DE | 4124299 | A1 | 1/1992 |
| DE | 69103295 | T2 | 12/1994 |
| DE | 69017784 | T2 | 11/1995 |
| DE | 19535781 | A1 | 3/1997 |
| DE | 19711935 | A1 | 4/1998 |
| DE | 29804046 | U1 | 4/1998 |
| DE | 69407869 | T2 | 4/1998 |
| DE | 69427390 | T2 | 9/2001 |
| DE | 100 59 714 | C1 | 5/2002 |
| DE | 10108810 | A1 | 8/2002 |
| DE | 10155011 | A1 | 5/2003 |
| DE | 69431204 | T2 | 8/2003 |
| DE | 10336902 | B3 | 8/2004 |
| DE | 102010011998 | A1 | 9/2010 |
| EP | 0480102 | A1 | 4/1992 |
| EP | 0560000 | A2 | 9/1993 |
| EP | 0629412 | A2 | 12/1994 |
| EP | 0768091 | A1 | 4/1997 |
| EP | 0884064 | A2 | 12/1998 |
| EP | 0914171 | A2 | 5/1999 |
| EP | 0916359 | A1 | 5/1999 |
| EP | 951302 | A2 | 10/1999 |
| EP | 1019117 | A1 | 7/2000 |
| EP | 1066851 | A1 | 1/2001 |
| EP | 1114648 | A2 | 7/2001 |
| EP | 1337288 | A1 | 8/2003 |
| EP | 1651290 | A1 | 5/2006 |
| EP | 2218469 | A1 | 8/2010 |
| EP | 2229965 | A1 | 9/2010 |
| EP | 2301598 | A1 | 3/2011 |
| EP | 2308524 | A1 | 4/2011 |
| EP | 2343091 | A1 | 7/2011 |
| EP | 2345440 | A1 | 7/2011 |
| EP | 2366412 | A2 | 9/2011 |
| EP | 2497521 | A1 | 9/2012 |
| EP | 2606919 | A1 | 6/2013 |
| EP | 2606920 | A1 | 6/2013 |
| EP | 2607712 | A1 | 6/2013 |
| GB | 2239675 | A | 7/1991 |
| RU | 2229899 | C2 | 6/2004 |
| WO | WO-9202263 | A1 | 2/1992 |
| WO | WO-9302732 | A1 | 2/1993 |
| WO | WO-9303786 | A1 | 3/1993 |
| WO | WO-9314805 | A1 | 8/1993 |
| WO | WO-9401148 | A1 | 1/1994 |
| WO | WO-9405347 | A1 | 3/1994 |
| WO | WO-9409835 | A1 | 5/1994 |
| WO | WO-9420165 | A2 | 9/1994 |
| WO | WO-9523000 | A2 | 8/1995 |
| WO | WO-9618358 | A1 | 6/1996 |
| WO | WO-9625969 | A2 | 8/1996 |
| WO | WO-9744071 | A1 | 11/1997 |
| WO | WO-9853864 | A1 | 12/1998 |
| WO | WO-9919017 | A1 | 4/1999 |
| WO | WO-0027446 | A1 | 5/2000 |
| WO | WO-0043054 | A2 | 7/2000 |
| WO | WO-0062842 | A1 | 10/2000 |
| WO | WO-0107760 | | 2/2001 |
| WO | WO-0107787 | | 2/2001 |
| WO | WO-0183016 | | 11/2001 |
| WO | WO-03057013 | | 7/2003 |
| WO | WO-03103745 | | 12/2003 |
| WO | WO-2005002646 | A1 | 1/2005 |
| WO | WO-2005016416 | A1 | 2/2005 |
| WO | WO-2005021078 | A1 | 3/2005 |
| WO | WO-2005030316 | A1 | 4/2005 |
| WO | WO-2005032620 | A1 | 4/2005 |
| WO | WO-2005081681 | A2 | 9/2005 |
| WO | WO-2006020942 | A1 | 2/2006 |
| WO | WO-2006034158 | A2 | 3/2006 |
| WO | WO 2006/051023 | | 5/2006 |
| WO | WO-2006133209 | A1 | 12/2006 |
| WO | WO-2007003351 | A1 | 1/2007 |
| WO | WO-2007103390 | A2 | 9/2007 |
| WO | WO-2007103464 | A2 | 9/2007 |
| WO | WO-2007112033 | A2 | 10/2007 |
| WO | WO-2008017289 | A2 | 2/2008 |
| WO | WO-2008034068 | A2 | 3/2008 |
| WO | WO-2008054699 | A2 | 5/2008 |
| WO | WO-2008106103 | A2 | 9/2008 |
| WO | WO-2008116765 | A2 | 10/2008 |
| WO | WO-2008124696 | A1 | 10/2008 |
| WO | WO-2008137352 | A1 | 11/2008 |
| WO | WO-2008137353 | A1 | 11/2008 |
| WO | WO-2009015784 | A1 | 2/2009 |
| WO | WO-2010133567 | A1 | 11/2010 |
| WO | WO-2013034547 | A1 | 3/2013 |
| WO | WO-2013092971 | A1 | 6/2013 |
| WO | WO-2013093001 | A2 | 6/2013 |
| WO | WO-2013093058 | A1 | 6/2013 |

* cited by examiner

CATHETER DEVICE HAVING A CATHETER AND AN ACTUATION DEVICE

CROSS-REFERENCE TO RELATED APPLICATIONS

This application is a continuation of U.S. patent application Ser. No. 13/147,880, now U.S. Pat. No. 9,089,670, which entered the national stage on Oct. 13, 2011 and which is a United States National Stage filing under 35 U.S.C. §371 of International Application No. PCT/EP2010/000952, now expired, filed Feb. 3, 2010, which claims the benefit of U.S. Provisional Patent Application No. 61/149,753, filed Feb. 4, 2009, and European Patent Application No. 09075053.0, now expired, filed Feb. 4, 2009, the contents of all of which are incorporated by reference herein in their entirety. International Application No. PCT/EP2010/000952 was published under PCT Article 21(2) in English.

The invention resides in the field of medical equipment and can be used advantageously in particular in operations on the human or animal body.

The invention relates in detail to a catheter device which has a catheter to be introduced and also additional elements which ensure optimised usability of the catheter device.

A catheter of this type can be introduced through an entry opening into a naturally occurring vessel of the body or a tube, for example a blood vessel or a ureter, in order to perform specific desired functions in a minimally invasive manner. At the end of the catheter a functional element which allows specific operations by remote control can be provided.

The problem often resides in bringing firstly the functional element by means of the catheter to the correct place in the body without damaging body regions en route beyond an acceptable extent. For this purpose, the functional element can be either covered or deformed during introduction such that the introduction is made possible without damage or at least made easier.

A number of catheter devices is already known from the state of the art.

An intracardial pump device with a catheter is known from the German patent specification DE 103 36 902 B3, which catheter carries a pump in its end region. This can basically have a larger diameter, to a limited degree, than the catheter but the pump must be introduced and removed surgically in the case of too large a diameter since it is basically invariable in diameter.

From the German patent specification DE 100 59 714 C1, a pump is known for introduction into a blood vessel of a body, the pump discharging at the distal end into a cannula, the diameter of which is variable. For example, the cannula is situated during introduction into the blood vessel in a compressed state which is assumed, as a function of the temperature, in a range of low temperatures. If the cannula is inserted into the body, then it heats to body temperature and thereby assumes a second, expanded shape because of the shape memory of the material thereof. The cannula can comprise for this purpose for example Nitinol, a known material with shape memory properties. Any possibilities of transferring a cannula widened in this manner again into the compressed state in order to be able to withdraw the pump and the catheter without surgical intervention are not referred to in the mentioned document.

A catheter device with a pump is known from WO 94/05347, in which a pump housing and possibly also the pump blades can be radially deployed by relative longitudinal displacement of a drive shaft relative to a sleeve directly surrounding the latter.

Against the background of the state of the art, the object is set of producing a catheter device by as simple and economical constructional means as possible, which catheter device allows optimised introduction and removal of the catheter with as little damage as possible and thereby obtains an as large as possible clear transit channel of the catheter.

The object is achieved according to the invention by the features of patent claim 1.

The invention thereby provides a catheter device, having a catheter, an actuation device at a first end of the catheter, a drive element inside the catheter for driving the actuation device, for example the drive element being a flexible shaft that drives a pump rotor in the actuation device if the actuation device is a pump and the catheter device also having a mechanical transmission element for transmitting a movement along the catheter to the actuation device, the actuation device having a coupling element which is connected to the transmission element and can be actuated by the latter relative to the longitudinal direction of the catheter in a first degree of freedom, and also a conversion element which can be actuated by the coupling element and which converts the actuation movement at least partially into a movement in a second degree of freedom.

The catheter according to the invention, which preferably entirely comprises biocompatible material/materials, can hence be introduced through an opening into a body and thereupon a movement can be transmitted by the transmission element to the actuatable coupling element. Such a movement can be effected for example in the longitudinal direction of the catheter in the form of pushing or pulling, or in the form of a rotation about the longitudinal direction of the catheter if the transmission element allows transmission of a rotary movement, for example if the transmission element is configured as a hose inside the catheter, for example surrounding a flexible shaft or surrounding the catheter.

The movement transmitted to the coupling element in the first degree of freedom is transmitted from the latter to a conversion element which converts the actuation movement into a movement in a second degree of freedom. The movement in the first degree of freedom can thereby be retained in addition for the entire movement of the conversion element and the actuation device.

For example, the conversion element can have a link guide or a similar device, such as for example a worm, for converting between a movement in the longitudinal direction of the catheter and a rotary movement about the longitudinal direction. In this case, for example a pulling or pushing movement along the catheter can be converted into a rotary movement or vice versa.

Advantageously, the link guide can have a link track and a link block, at least one of these elements, in particular the link block, being connected rigidly to the catheter in the form of a guide pin. In this way, in particular a pushing or pulling movement applied by cables along the catheter can cause a corresponding movement of the coupling element along the catheter, which movement for its part produces a rotary-thrusting movement of the conversion element. An advantage of the invention in this case resides in the fact that the rotary component of the movement need not be transmitted along the entire catheter but instead is produced only at the end of the catheter by the conversion element.

The rotary-thrusting movement at the end of the catheter can be used advantageously in that it is transmitted to a protective cap which protects a functional element at the end of the catheter and can be applied particularly easily by means of the rotary-thrusting movement.

If the transition element is intended in particular to transmit a movement in the longitudinal direction of the catheter, then it can be configured as a cable, in particular in the manner of a Bowden cable, or as a group of cables which are connected to the coupling element, extend along the catheter, in particular on the outside thereof, and can be actuated from outside after introduction of the catheter into a vessel. The cables are advantageously guided individually on or in the catheter in a longitudinally displaceable manner, for example in that they are recessed at least partially in the wall of the catheter.

It can also be provided that the cable or cables are guided in guide devices on the outside of the catheter, such as for example external rings.

If the transmission element is configured as a cable or group of cables, then these are advantageously fixed individually on a common fixing element taking into account the longitudinal adaptations which are required by the given curvature of the catheter. The fixing element can be formed for example by the cooperation of two rings, between which the individual cables can be firmly clamped after the catheter is introduced. The group of cables can thereafter be moved uniformly by manipulation of the fixing element.

At the end of the catheter which is situated opposite the fixing element and on which the transmission element is connected to the coupling element, the latter can be configured as a bearing ring to which the conversion element is connected rotatably. It is consequently ensured that, in the case where the conversion element performs a rotary movement, this is not transmitted to the coupling element and the cables or in general the transmission element. The transmission element can hence perform purely a movement in the longitudinal direction of the catheter.

Conversely, also the transmission element can be configured as a hose or tubular element and be designed to transmit a rotary movement about the longitudinal direction of the catheter. In this case, the rotary movement is transmitted to the conversion element which converts this into a movement in the longitudinal direction of the catheter. It is advantageously ensured in this case that the conversion element is displaceable in the longitudinal direction of the catheter relative to the coupling element, for example in that the coupling element and the conversion element are introduced one into the other in a telescopic manner.

The catheter device can advantageously be configured such that a lock is provided for guiding the catheter through an opening, the lock having, on the side orientated towards the actuation device, a shape which retains the coupling element during withdrawal of the catheter and consequently produces a rotary movement of the conversion element.

If the catheter is removed, i.e. withdrawn for example from a blood vessel, then it should be ensured that the functional element is protected in that for example a cap is pushed onto the functional element by means of the actuation device. For this purpose, it is ensured by means of the lock that the transmission element also effects a thrusting movement during withdrawal of the catheter, which movement is converted on the actuation device by the conversion device into the desired combination movement for placing on a protective cap.

It can be ensured for this purpose that, during further withdrawal of the catheter, the lock is jointly removed or that, after actuation of the transmission element, the latter can be moved through the lock.

A particularly favourable and advantageous use of the catheter device is characterised by a functional element, in particular a pump, at the end of the catheter and also a protective cap which is connected to the conversion element and which receives the functional element in a first position of the conversion element and releases said functional element in a second position.

If the protective cap has smaller inner dimensions than the outer dimensions of the functional element in the released position and the functional element can be compressed at least partially, the functional element can, on the one hand, be compressed by the actuation device through the catheter device according to the invention when removing said functional element and, on the other hand, if the actuation device assumes its second position, the functional element can be released in order to expand. Corresponding expansion movements can be achieved for example by using so-called temperature memory alloys or in that for example pump blades expand automatically into an operating state during rotary operation of a functional element configured as a pump.

An advantageous method for introduction according to the invention of a catheter device which is configured according to the invention provides that firstly the catheter is introduced, the actuation device being situated in a first position, and that thereupon the coupling element and the conversion element are actuated by means of the transmission element in order to release a functional element by means of the actuation device in the second position thereof. Hence, it is ensured in a simple manner, not particularly susceptible to faults, that a catheter can be introduced with an expandable functional element or a functional device with a low risk of injury into a vessel of a patient and thereafter can be expanded in the desired manner. As a result of the construction according to the invention, also functional faults are minimised during removal of the catheter device.

Figure 2:
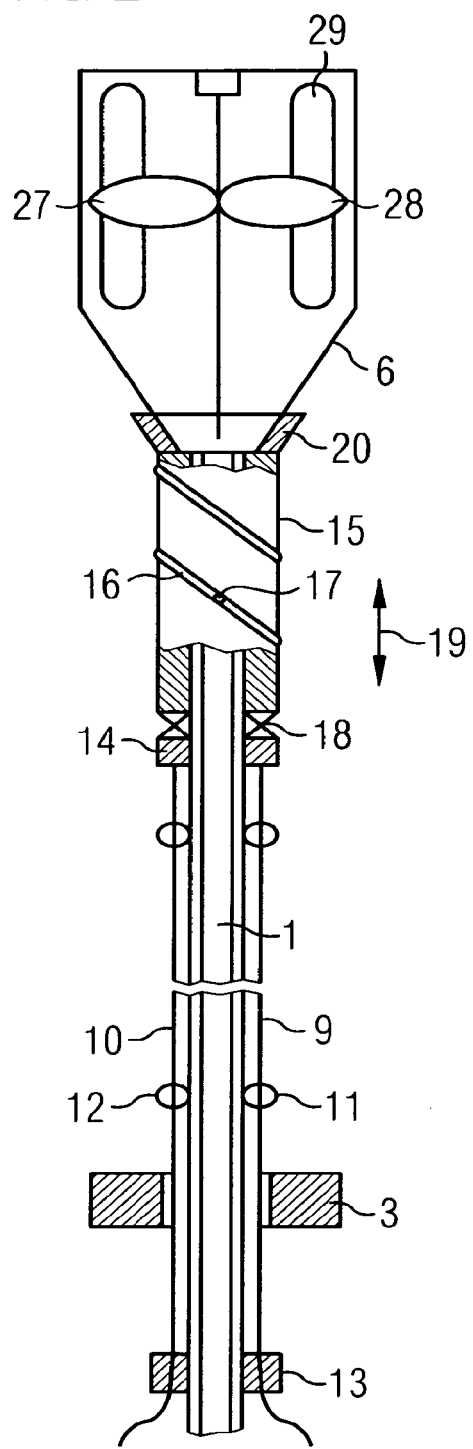

In the following, the invention is shown and subsequently described with reference to an embodiment in a drawing with reference to several Figures. There are thereby shown FIG. 1 schematically, a catheter introduced into a blood vessel, the end of the catheter being situated in the volume of a ventricle, FIG. 2 schematically, in longitudinal section, a catheter having an actuation device and a functional element, FIG. 3 in longitudinal section, a device for fixing cables, FIG. 4 an alternative device to that shown in FIG. 3, FIG. 5 the actuation device enlarged in longitudinal section with a part of a functional element and also FIG. 6 the actuation device schematically in a cross-section.

In the embodiment, the application of the invention to a catheter is described in particular, which catheter carries a pump at the end thereof and can be introduced into the bloodstream of a patient.

Pumps of this type which are introduced for example into the heart of a patient and serve to convey blood for supporting the heart are basically known. It is thereby also known to construct such pump structures such that they can be widened in diameter after introduction into the ventricle.

It is sensible and essentially an application advantage of the present invention to provide thereby a mechanism which can release the functional element which, in the present case, comprises the pump so that it is potentially widened automatically and can also compress in order to be able to remove the functional element/the pump with the catheter again from the body. In the interim, the entire device should advantageously remain in the body and should neither damage the patient in this state nor impede the flow of blood through the catheter beyond a tolerable degree.

Basically, the catheter 1 which is represented merely schematically in FIG. 1 is introduced through an incision 2 by means of a lock 3 into the blood vessel, is pushed through the latter until the end 5 of the catheter with the functional element 6 that can be rotatably driven by the flexible shaft 4 is positioned in the ventricle 7 and is fixed in this state, and the actuation device 8, which will be dealt with further on in more detail, can be actuated in order to release the functional element 6 by means of a transmission element. The flexible shaft 4 may be connected at its proximal end to a motor located outside the body.

In FIG. 2, the transmission element and also the actuation device and the functional element are described in more detail. FIG. 2 shows in longitudinal section a catheter 1 which is surrounded by a group of cables 9, 10 which extend parallel to each other in the longitudinal direction of the catheter 1 at the circumference thereof and parallel to a flexible shaft 4 if such a shaft is used for driving a functional element like a pump rotor at the end of the catheter. In order to guide the cables 9, 10, these can be recessed entirely or partially in the wall of the catheter 1 moveably in the longitudinal direction or can be guided through guide devices 11, 12 in the form of openings or loops on the circumference of the catheter. If the cables are sufficiently rigid and the guide devices 11, 12 are set sufficiently narrowly, also a thrusting movement can be achieved by means of the cables in addition to a pulling movement.

On the other hand, it is conceivable as an alternative to replace the cables by a hose which surrounds the catheter 1 concentrically and likewise can serve for transmitting pulling and thrusting movements. For this purpose, the hose should be provided with corresponding axial compression strength without the bending rigidity being significantly increased. Corresponding technologies are adequately known industrially and already used.

Basically, also the production of the transmission element by a single cable at the circumference of the catheter is conceivable. The arrangement of cables on the outside of the catheter or at least partially in the wall of the catheter is thereby preferred, however, in particular with a small number of cables, also guidance thereof within the catheter or a hose inside the catheter is basically conceivable.

The cables 9, 10 are mounted together, for example by clamping, on the fixing element 13. Hence the entirety of cables can be moved in the same direction and to the same extent by manipulation of the fixing element 13. The fixing element is dealt with below in even more detail.

In addition, a coupling element 14 which is configured there as a bearing ring which is displaceable in the longitudinal direction of the catheter is evident in FIG. 2. Cables 9, 10 are fitted on this bearing ring 14 so that pulling or pushing movements of the cables are transmitted firstly to the bearing ring 14.

On the other hand, the conversion element 15 in the form of a cylinder provided with one or more link tracks 16 is connected to the bearing ring 14. The coupling element 14 transmits pulling and thrusting movements to the cylinder 15, in the link track of which a guide pin 17 which forms a link block is guided. The cylinder 15 is consequently forced onto a screw-like movement track since the guide pin 17 is fixed in the catheter 1.

In order that the conversion element 15 can rotate independently of the bearing ring 14, a rotary bearing 18, for example in the form of a sliding bearing, is provided between these two elements, said sliding bearing being able to transmit the thrusting and pulling forces.

If the cables 9, 10 are actuated, then a thrusting movement in the direction of the arrow 19 is produced for the bearing ring 14 just as for the cylinder 15 and is superimposed in addition by a rotary movement through the link guide in the case of the cylinder 15.

In FIG. 2, a blood pump is represented as functional element 6 at the end of the catheter 1, which blood pump is widened relative to the diameter of the catheter or of the actuation device. This is possible in that the mentioned functional element can assume an expanded and a compressed situation, it being able to be received at least partially in the compressed situation by a protective cap 20 at the end of the actuation element 14, 15.

If the conversion element 15 together with the protective cap 20 is withdrawn by the cables 9, 10 in a screw-like movement, then the pump 6 can widen in diameter, whilst it is compressed during a thrusting movement of the cables 9, 10 by the screw movement of the cap 20 and is received at least partially in the cap.

In addition, it becomes clear by the representation of FIG. 2 that, when removing the catheter from the incision, the lock 30 consequently plays a special role in that the thrusting movement of the protective cap 20 is introduced or ended at the latest when the bearing ring 14 strikes the lock 3 so that the functional element is present in a completely compressed form at least when passing through the incision.

The pump is configured in particular for the purposes of compressibility, the rotor blades of the pump for example being able to be folded in and the housing being able to be collapsed, for example by the production from a so-called temperature memory material, an alloy which can assume different shapes at different temperatures. An elastically compressible construction is likewise conceivable, which can be opened up or closed merely by the force effect and/or by the effect of the conveyed fluid into the desired position.

Figure 3:
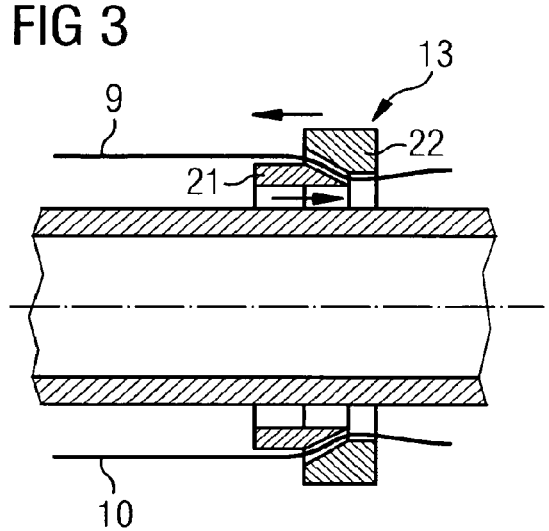

FIG. 3 shows a fixing element 13 in the form of two conical rings 21, 22, between which the cables 9, 10 can be clamped by axial compression of the rings. Since the cables are fixed individually, length differences which are produced by curvature of the catheter and a correspondingly different length requirement of the cables situated radially inwards or outwards, can be compensated for. The fixing element in this case should fix the cables after introduction of the catheter. Thereafter, the group of cables can be actuated together by means of the fixing element.

Figure 4:
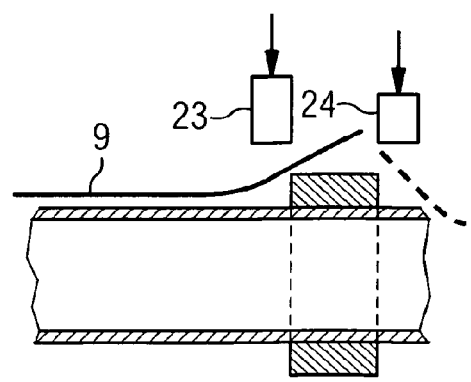

Another embodiment variant of the fixing element is represented in FIG. 4, in which the cables 9, 10 can be fixed with a squeezing or bending movement by means of correspondingly moveable elements 23, 24.

Figure 5:
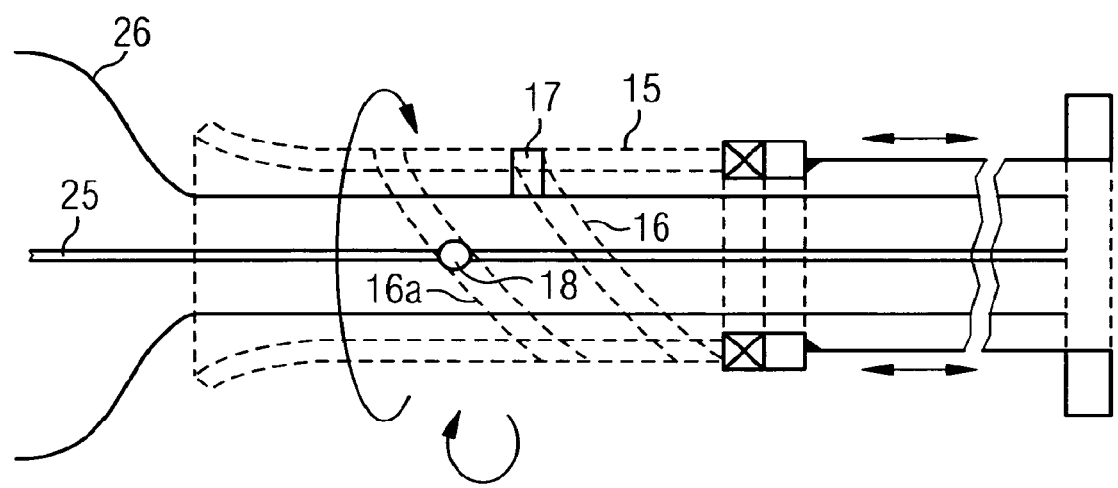

The mode of operation of the conversion element 15 emerges from FIG. 5 in more detail than from FIG. 2, a plurality of guide pins 17, 17a being represented there, said guide pins being mounted respectively on the catheter 1 and being able to run in different, parallel, screw-like link tracks 16, 16a which are offset relative to each other.

The protective cap 20 at the end of the conversion device 15 can be integrated in the latter or connected to the latter.

It should be mentioned in addition that a shaft 25 can be provided within the catheter 1, which serves to drive the pump 6 and is mounted in the pump housing 26. By means of the shaft 25, rotor blades 27, 28 are actuated and blood is conveyed for example through the openings 29 in the pump housing 26. According to the design of the rotor/of the pump, also an inflow towards the rotor through the openings 29 in the pump housing 26 is possible and an axial outflow or an axial inflow and outflow.

Figure 6:
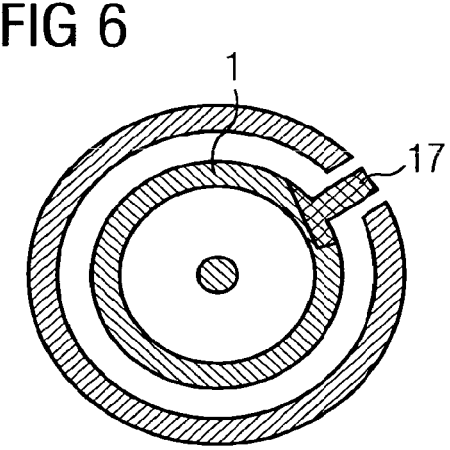

In FIG. 6, a cross-section through the catheter in the region of the actuation device is shown, the guide pin/guide block 17 integrated in the catheter 1 being represented. The guide pin 17 can either be cast in or glued into the catheter and/or even comprise the material of the catheter 1 and also be configured in one piece with the catheter. The catheter should comprise a flexible but solid plastic material which ensures a constant cross-section of the catheter. If a hose is used as transmission element, then the latter can comprise the same material as the catheter. If cables are used, then these must comprise a high-strength biocompatible material, such as for example special steel, platinum or silver wire or specific plastic materials. The cables can be provided with a locking device in order to allow fixing at different lengths respectively according to the present curvature of the catheter on the fixing element.

By means of the screw-like movement of the actuation device produced with the invention, pushing a protective cap onto the functional element is substantially facilitated already with respect to the more favourable friction conditions. By applying a thread-like surface structure on the outside of the functional element, i.e. in particular on the pump housing and/or on the inside of the protective cap, the compression movement can in addition be facilitated.

The invention hence ensures simple and reliable actuation of an actuation device for protecting a functional element during positioning of the catheter in a sensitive region within the body of a patient.

The invention claimed is:

1. A catheter device, comprising:
a catheter;
a drive element extending through the catheter;
a hose surrounding the catheter, a distal end of the hose comprising a protective cap;
an actuation device at a first end of the catheter, wherein the actuation device comprises:
a pump rotor; and
a blood pump housing enclosing the pump rotor, wherein the blood pump housing is expandable and compressible and wherein the protective cap is flared distally and configured to at least partially compress the blood pump housing;
wherein the hose comprises a mechanical transmission element for transmitting a first movement along the catheter to the actuation device, the actuation device having a coupling element which is connected to the transmission element and can be actuated by the transmission element along a longitudinal direction of the catheter; and
a conversion element which can be actuated by the coupling element and which converts a first movement at least partially into a second movement.

2. The catheter device according to claim 1, wherein the conversion element has a device, in particular a link guide, for converting between a movement in the longitudinal direction of the catheter and a rotary movement about the longitudinal direction.

3. The catheter device according to claim 2, wherein the link guide has a link track and a link block, at least one of the elements being connected rigidly to the catheter.

4. The catheter device according to claim 1, wherein the transmission element is designed to transmit a movement in the longitudinal direction of the catheter.

5. The catheter device according to claim 1, wherein the conversion element produces a rotary movement about the longitudinal direction of the catheter in the region of the actuation device.

6. The catheter device according to claim 1, wherein the connection between the coupling element and the conversion element provides a moveable mounting which enables a relative movement of the coupling element and of the conversion element in the second degree of freedom.

7. The catheter device according to claim 6, wherein the coupling element is configured as a bearing ring to which the conversion element is connected rotatably.

8. The catheter device according to claim 1, wherein the transmission element is configured as at least one cable which is guided parallel or in a helix-like manner relative to the catheter, on the outside thereof.

9. The catheter device according to claim 8, wherein the cables are guided individually on the catheter, displaceably in the longitudinal direction.

10. The catheter device according to claim 9, wherein the cables are recessed at least partially in the wall of the catheter.

11. The catheter device according to claim 8, wherein the cables are fixed individually on a common fixing element, taking into account any required length adaptations due to a given curvature of the catheter.

12. A method for introducing a catheter device according to claim 1, characterized in that firstly the catheter is introduced, the actuation device being situated in a first position, and in that thereupon the coupling element and the conversion element are actuated by means of the transmission element in order to release a pump rotor by means of the actuation device in the second position thereof.

13. The catheter device according to claim 1, wherein the pump rotor comprises blades which expand from a first compressed state into an operating state during rotation.

14. The catheter device according to claim 13, wherein the protective cap has smaller inner dimensions than an outer dimension of the pump rotor in an expanded state.

15. The catheter device according to claim 14, wherein the second movement releases the blood pump housing from the protective cap and hose and the blood pump housing is expanded.

16. The catheter device according to claim 1, wherein the protective cap is coupled to the conversion element.

17. The catheter device according to claim 16, wherein the blood pump housing comprises a memory alloy.

* * * * *